United States Patent [19]

Rasmusson

[11] Patent Number: 4,938,765
[45] Date of Patent: Jul. 3, 1990

[54] SURGICAL SILICON LOOPS

[75] Inventor: Larry A. Rasmusson, Coon Rapids, Minn.

[73] Assignee: Life Centers, Inc., Bloomington, Minn.

[21] Appl. No.: 370,349

[22] Filed: Jun. 22, 1989

[51] Int. Cl.⁵ ............................................. A61B 17/12
[52] U.S. Cl. .................................................... 606/158
[58] Field of Search ................ 606/158, 157, 151, 203, 606/111

[56] References Cited

U.S. PATENT DOCUMENTS

| | | | |
|---|---|---|---|
| 1,252,260 | 1/1918 | Gilberg | 606/203 |
| 2,113,534 | 4/1938 | Brown | 606/203 |
| 2,803,253 | 8/1957 | Campbell, III | 606/203 |
| 2,936,759 | 5/1960 | Yuhas | 606/203 |
| 3,762,418 | 10/1973 | Wasson | 606/158 X |
| 3,880,166 | 4/1975 | Fogarty | 606/158 |
| 3,910,280 | 10/1975 | Talonn | 606/158 |
| 3,993,076 | 11/1976 | Fogarty | 606/158 |
| 4,069,825 | 1/1978 | Akiyama | 606/158 |
| 4,188,953 | 2/1980 | Klieman et al. | 606/158 |
| 4,611,593 | 9/1986 | Fogarty et al. | 606/158 |
| 4,708,140 | 11/1987 | Baron | 606/158 |

*Primary Examiner*—Mickey Yu
*Attorney, Agent, or Firm*—Merchant, Gould, Smith, Edell, Welter & Schmidt

[57] ABSTRACT

A vessel occluding loop 10 for occluding the flow of blood in a vessel 30 is disclosed. The loop 10 has an elongate body having an outer surface. The outer surface has a plurality of elongate engaging surfaces 11. The engaging surfaces 11 define a generally planar area of contact for contact with a blood vessel. The engaging surfaces have a first member 12, a second member 13, and third member 14 which form the preferably planar engaging surface. Depressed zones 18 and 19 are formed between the members, wherein the blood vessel may enter the depressed zones 18 and 19 when the loop is wrapped around the blood vessel 30, thereby increasing traction.

7 Claims, 2 Drawing Sheets

SURGICAL SILICON LOOPS

BACKGROUND OF THE INVENTION

1. Field of the Invention

This invention relates generally to surgical loops used in occluding blood vessels during surgery and more particularly to a loop having a flat or plurality of flat engaging surfaces.

2. Description of the Prior Art

During surgery, it is often necessary to occlude the flow of blood through a blood vessel. Such occlusion may be accomplished by means of a vessel occluding instrument, such as that described in U.S. Pat. Nos. 4,611,593; 3,880,166; and 3,993,076. In addition to the use of vessel occluding instruments, it is also a well known practice to use silicon loops to occlude the flow of blood. Such silicon loops are also utilized in the vessel occluding instruments described in the previously mentioned patents and are referred to as "tape" in these patents.

The loops that have been used to date typically have either a circular or elliptical cross section. While such loops have typically been adequate, the loops have had a tendency to slip when wrapped around a blood vessel, especially when the blood vessel is wet or covered with blood.

The present invention addresses the problems associated with the prior art loops and provides for a loop which reduces the pinching of blood vessels as well as increasing the traction and thus reducing slippage of the loop while wrapped around the blood vessel.

SUMMARY OF THE INVENTION

Figure 1:
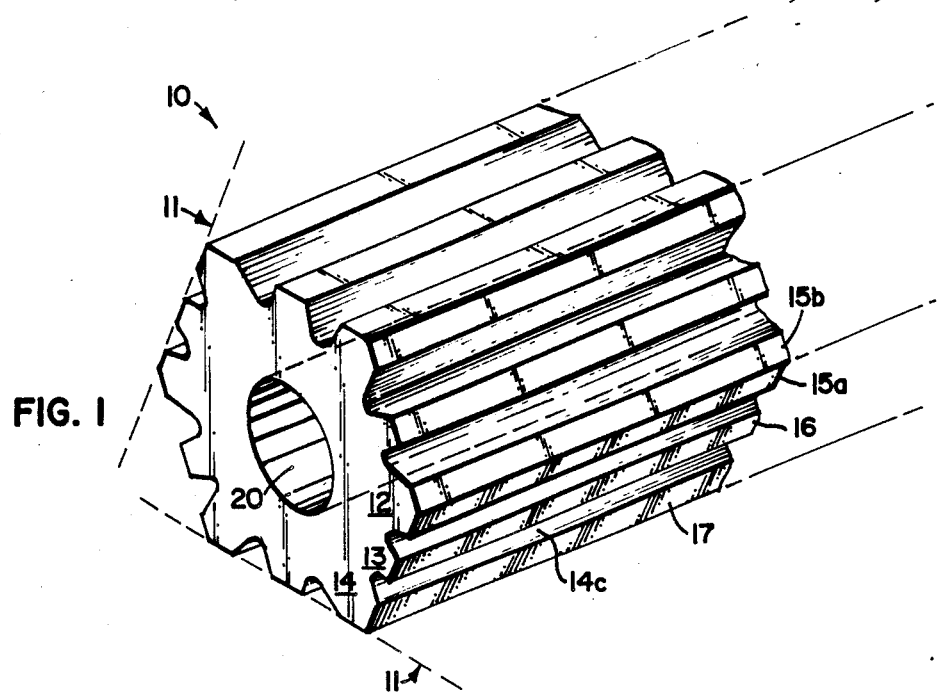
FIG. 1 is a perspective view of the surgical vessel loop of the present invention.
Figure 3:
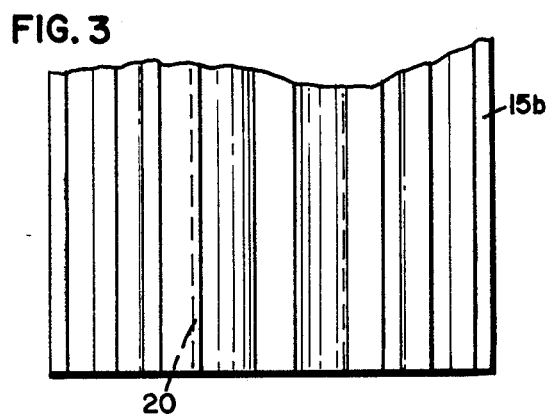
FIG. 3 is a top plan view of the vessel loop of FIG. 1, the bottom loop being a mirror image thereof.
Figure 2:
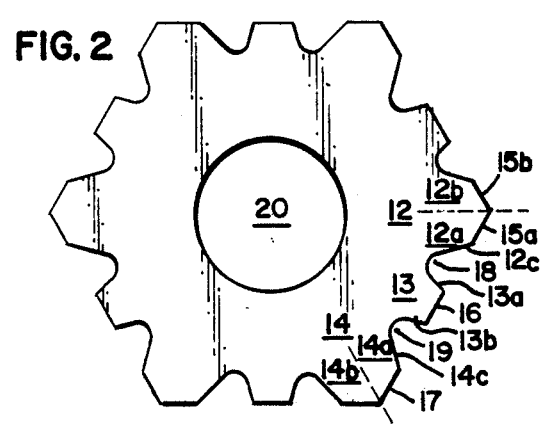
FIG. 2 is a left side elevational view of the vessel loop of FIG. 1, the right side elevational view being a mirror image thereof.
Figure 4:
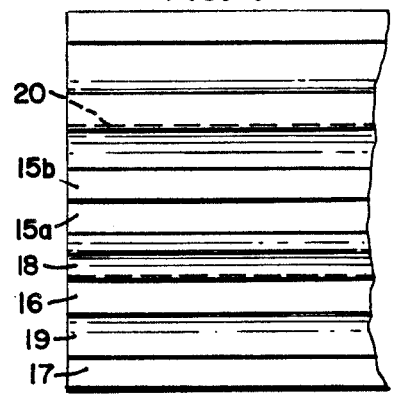
FIG. 4 is a front elevational view of the loop of FIG. 1, the rear elevation view being a mirror image thereof.
Figure 5:
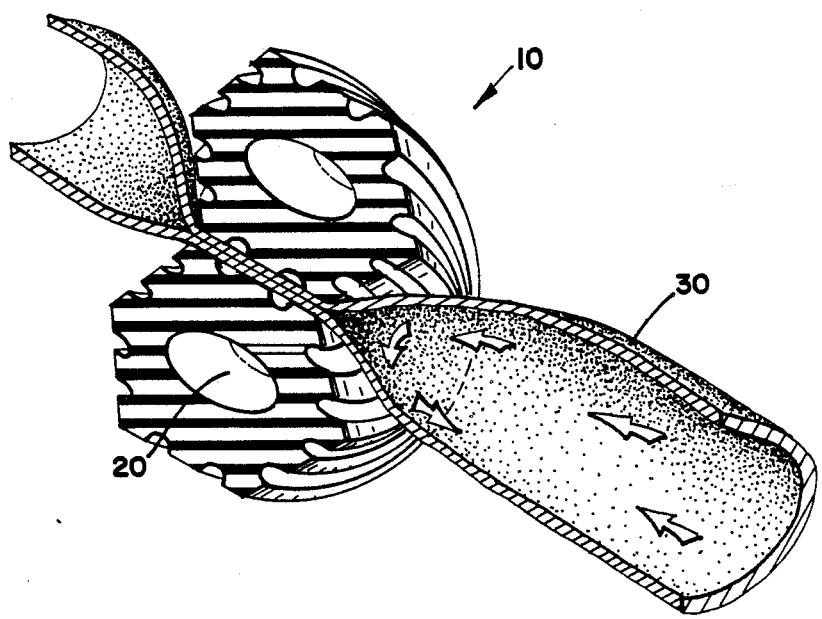
FIG. 5 is a cross sectional view of the vessel loop of FIG. 1 which has been wrapped around the blood vessel.

The present invention is a vessel occluding loop for occluding flow of blood in a vessel. The loop has an elongate body having an outer surface. The outer surface has a plurality of elongate engaging surfaces. Each engaging surface defines a generally planar area of contact for contact with a blood vessel. In a preferred embodiment, the loop has at least six engaging surfaces around the loop's periphery. The engaging surfaces, in a preferred embodiment, each comprise a plurality of members. The members have a top and the tops of the members form the engaging surface. Preferably, the tops of the members have a planar top. Also in a preferred embodiment, the engaging surface has a depressed zone formed between the members, wherein the blood vessel may enter the depressed zone when the loop is wrapped around the blood vessel, thereby increasing traction.

DETAILED DESCRIPTION OF THE INVENTION

Referring to the drawings, wherein like numerals represent like parts throughout the several views, there is generally disclosed at 10 a vessel occluding loop. The loop 10 is an elongate extrusion of a medical grade silicon material and may be extruded to any suitable length. It is understood that other suitable, flexible materials may be used. The loop 10, as shown in the drawings, has a generally circular cross section with a plurality of members 12, 13 and 14 positioned around the periphery of the loop. Further, the loop 10 is shown as having a generally hexagonal outer shape and generally has six engaging surfaces 11. The engaging surfaces 11 are generally similar and accordingly, only one of the engaging surfaces 11 will be discussed in detail, with the understanding that the other engaging surfaces 11 are similar.

A first member 12 extends outward on the periphery of the elongated body member and is a continuous protrusion along the body. The first member 12 has a first portion 12a and a second portion 12b. While the first member 12 is a single member, it is being described as having a first and second portion in that the first portion 12a is used to form one engaging surface 11 while the second portion 12b is used to form an adjacent engaging surface 11. The member 12 has a first top surface 15a and a second top surface 15b. The top surfaces 15a and 15b are planar. Because there are six engaging surfaces, the angle formed by the top surfaces 15a and 15b is 120°. The member 12 has a downwardly depending sidewall 12c. A second member 13 has a generally planar top surface 16 which is in the same plane as the top surface 15a. The second member 13 has a first downwardly depending side member 13a which is connected to the side 12c. A radius is formed where the two sections are joined. Similarly, the second section 13 has a downwardly depending second side 13b. A third member 14 has a first portion 14a and a second portion 14b. While similar to the first section 12, in that it is one section, the third member 14 is described as having a first portion 14a and a second portion 14b because the first portion 14a is used to form an engaging surface 11 while the second portion 14b is used to form an adjacent engaging surface. The first portion 14a has a planar top surface 17 which is generally on the same plane as the top surfaces 15a and 16. The generally downwardly depending side 14c is cooperatively connected to the side 13b. A first depressed area 18 is formed in the hollow formed between the first member 12 and the second member 13. Similarly, a second depressed area 19 is formed between the second member and the third member 14.

The members 12, 13 and 14 are continuous along the elongated body of the loop 10 and form ribs around the periphery of the loop.

It is understood that while it is preferred that the top surfaces 15a, 16 and 17 be planar and in the same plane, other variations and surface configurations may be utilized and still come within the scope of the present invention.

A longitudinal bore 20 extends through the elongate body of the loop 10. Or optionally, the center of the loop may be solid. The advantage of having the bore 20 extend through the loop is that an added air cushioning is achieved with the loop 10.

While various sizes of the various components may be utilized, the loop, as shown, has a diameter of 0.060 inches and a thickness of 0.140 inches. This results in an engaging surface 11 having a total width of 0.70 inches with each of the surfaces 15a, 16 and 17 having a width of 0.010 inches. The radius which is formed to connect the sidewalls of the member is typically 0.005 inches. One of the advantages of having 6 or more engaging surfaces 11 is that if the loop contacts the blood vessel 30 at the point at one of the first or third members, there is a tendency for the loop to roll and thereby have the three top surfaces 15a, 16 and 17 engage the vessel 30.

While it is also understood that the engaging surfaces 11 are shown as being non-continuous and having depressed zones, it is also envisioned that the engaging surfaces could be continuous and form one flat engaging surface. However, having the engaging surface 11 comprising three separate surface reduces the pinching and increases traction. The blood vessel 30 has a tendency to enter the depressed zones 18 and 19 when the loop 10 is wrapped around the blood vessel such that added traction is gained by the blood vessels entering the depressed zones 18 and 19. If the engaging surface 11 was flat, this would not occur. In manufacturing the loop, it may simply be continuously extruded as a unitary piece and cut to appropriate lengths.

In use, the loop 10 is simply wrapped around the blood vessel 30, tightened and secured by suitable means. The opening in the blood vessel is then constricted and blood does not flow through the blood vessel 30. The aforementioned design of the present invention with the arrangement of the members 12, 13 and 14 reduce the pinching of the vessel 30 while increasing traction and thus reducing slippage.

Other modifications of the invention will be apparent to those skilled in the art in light of the foregoing description. This description is intended to provide specific examples of individual embodiments which clearly disclose the present invention. Accordingly, the invention is not limited to these embodiments of the use of elements having specific configurations and shapes as presented herein. All alternative modifications and variations of the present invention which follow in the spirit and broad scope of the appended claims are included.

I claim:

1. A vessel occluding loop for occluding the flow of blood in a vessel, the loop having an elongate body having a bore formed through the length of the elongate body and having an outer surface, the outer surface having at least six engaging surface around the loops periphery, each engaging surface comprising a plurality of members, the members each having a top and the tops forming the engaging surface, each of the engaging surfaces have first, second and third members, the members each having a planar top, and a depressed zone formed between the members, wherein the blood vessel may be compressed to enter the depressed zone when the loop is wrapped around the blood vessel, thereby increasing traction.

2. A vessel occluding loop for occluding the flow of blood in a vessel, the loop having an elongate body having an outer surface, the outer surface having at least six elongate engaging surfaces, each engaging surface defining a generally planar area of contact for contact with a blood vessel.

3. The loop of claim 2, wherein each engaging surface comprises a plurality of members, the members each having a top and the tops forming the engaging surface.

4. The loop of claim 3, wherein each engaging surface comprises first, second and third members.

5. The loop of claim 3, wherein the members each have a planar top.

6. The loop of claim 1, wherein each engaging surface has a depressed zone, wherein the blood vessel may enter the depressed zone when the loop is wrapped around the blood vessel, thereby increasing traction.

7. The loop of claim 2, wherein the elongate body has a bore formed therein.

* * * * *